United States Patent
Leivseth et al.

(10) Patent No.: US 11,234,894 B2
(45) Date of Patent: *Feb. 1, 2022

(54) APPARATUS, SYSTEM, AND METHOD FOR TESTING AND EXERCISING THE PELVIC FLOOR MUSCULATURE

(71) Applicant: PELVITAL USA, INC., Plymouth, MN (US)

(72) Inventors: Gunnar Leivseth, Oslo (NO); Ole Jakob Olsen, Stathelle (NO)

(73) Assignee: PELVITAL USA, INC., Plymouth, MN (US)

( * ) Notice: Subject to any disclaimer, the term of this patent is extended or adjusted under 35 U.S.C. 154(b) by 1274 days.

This patent is subject to a terminal disclaimer.

(21) Appl. No.: 15/618,104

(22) Filed: Jun. 8, 2017

(65) Prior Publication Data
US 2017/0273860 A1 Sep. 28, 2017

Related U.S. Application Data

(63) Continuation of application No. 14/009,429, filed as application No. PCT/NO2012/050058 on Apr. 3, 2012, now Pat. No. 9,949,888.

(30) Foreign Application Priority Data

Apr. 5, 2011 (NO) .................................. 20110524

(51) Int. Cl.
*A61H 19/00* (2006.01)
*A61B 5/00* (2006.01)
(Continued)

(52) U.S. Cl.
CPC ............. *A61H 19/40* (2013.01); *A61B 5/227* (2013.01); *A63B 23/20* (2013.01);
(Continued)

(58) Field of Classification Search
CPC ........ A61H 19/40; A61B 5/227; A61B 23/20; A61B 24/0087; A61B 2562/0219; A61B 2225/20; A61B 2225/50; A61B 2230/60
See application file for complete search history.

(56) References Cited

U.S. PATENT DOCUMENTS 5,766,137 A * 6/1998 Omata ............... A61B 5/02007
600/587
5,782,745 A 7/1998 Benderev
(Continued)

FOREIGN PATENT DOCUMENTS

WO WO1997017908 A1 5/1997
WO WO2000047108 A1 8/2000
(Continued)

*Primary Examiner* — Timothy A Stanis
(74) *Attorney, Agent, or Firm* — Skaar Ulbrich Macari, PA

(57) ABSTRACT

An apparatus for testing and exercising pelvic floor musculature, the apparatus comprising an elongate housing adapted for a pelvic floor aperture. The housing accommodates an oscillator and an accelerometer connected to a signal processor configured for communicating signals representative of values read from the accelerometer. A result is calculated from an applied oscillation and a response measured, and used for characterizing the musculature. In one embodiment the frequency resulting in the greatest response from the musculature is measured, and this frequency is applied during exercise.

7 Claims, 4 Drawing Sheets

(51) Int. Cl.
*A63B 24/00* (2006.01)
*A61B 5/22* (2006.01)
*A63B 23/20* (2006.01)

(52) U.S. Cl.
CPC .. *A63B 24/0087* (2013.01); *A61B 2562/0219* (2013.01); *A63B 2220/40* (2013.01); *A63B 2220/51* (2013.01); *A63B 2220/64* (2013.01); *A63B 2220/80* (2013.01); *A63B 2225/20* (2013.01); *A63B 2225/50* (2013.01); *A63B 2230/60* (2013.01)

(56) References Cited

U.S. PATENT DOCUMENTS

| | | |
|---|---|---|
| 6,244,066 B1 | 6/2001 | LaRose |
| 6,428,467 B1 | 8/2002 | Benderev |
| 7,998,202 B2 | 8/2011 | Lesh |
| 8,360,954 B2 | 1/2013 | Kim |
| 8,369,953 B2 | 2/2013 | Peddicord |
| 8,784,345 B2 | 7/2014 | Peddicord |
| 8,818,512 B2 | 8/2014 | Peddicord |
| 8,840,571 B2 | 9/2014 | Egorov et al. |
| 10,039,929 B1 | 8/2018 | Milchovsky et al. |
| 2001/0051327 A1 | 12/2001 | Hatano et al. |
| 2002/0120219 A1 | 8/2002 | Hovland et al. |
| 2003/0220589 A1* | 11/2003 | Leivseth ............... A61B 5/227 600/591 |
| 2005/0256387 A1* | 11/2005 | Omata ................... A61B 5/202 600/382 |
| 2006/0036188 A1 | 2/2006 | Hoffman et al. |
| 2007/0112284 A1* | 5/2007 | Hoffman ............... A61B 5/053 600/591 |
| 2007/0287610 A1 | 12/2007 | Novak et al. |
| 2009/0056445 A1 | 3/2009 | Veltink |
| 2010/0174214 A1 | 7/2010 | Gabbay et al. |
| 2010/0174218 A1* | 7/2010 | Shim ..................... A61B 5/224 601/84 |
| 2012/0265049 A1 | 10/2012 | Iglesias |
| 2014/0257268 A1 | 9/2014 | Sachs et al. |
| 2014/0296705 A1 | 10/2014 | Iglesias |
| 2014/0309550 A1 | 10/2014 | Iglesias |
| 2015/0032030 A1 | 1/2015 | Iglesias |
| 2015/0112231 A1 | 4/2015 | Iglesias |
| 2015/0165241 A1 | 6/2015 | Burdette |
| 2015/0290453 A1 | 10/2015 | Tyler et al. |
| 2016/0228324 A1 | 8/2016 | Garteiser et al. |
| 2016/0346610 A1 | 12/2016 | Iglesias et al. |

FOREIGN PATENT DOCUMENTS

| | | |
|---|---|---|
| WO | WO2001037732 A1 | 5/2001 |
| WO | WO2003097177 A1 | 11/2003 |
| WO | WO2010131252 A3 | 1/2010 |
| WO | WO2011050252 A1 | 4/2011 |
| WO | WO2013147992 A1 | 10/2013 |

* cited by examiner

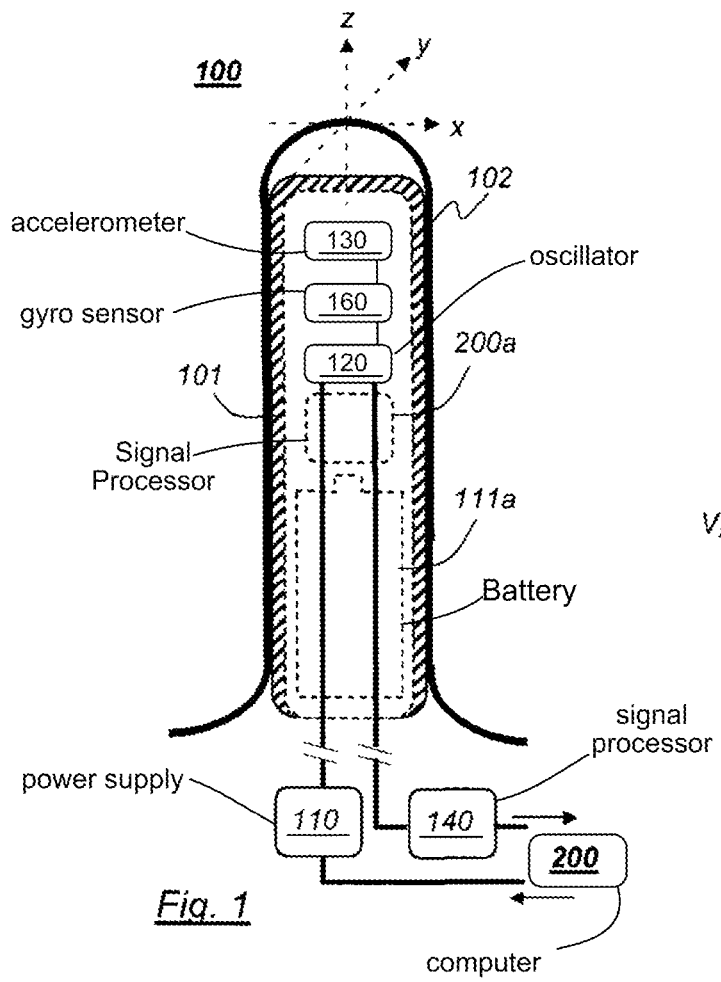
Fig. 1
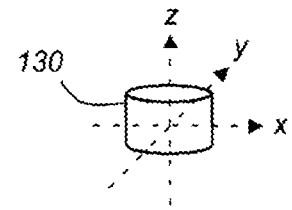
Fig. 2: Prior Art
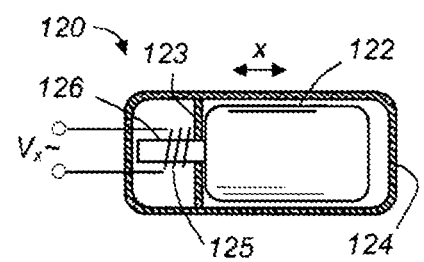
Fig. 3: Prior Art
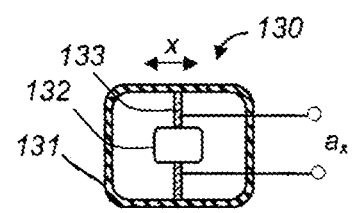
Fig. 4: Prior Art
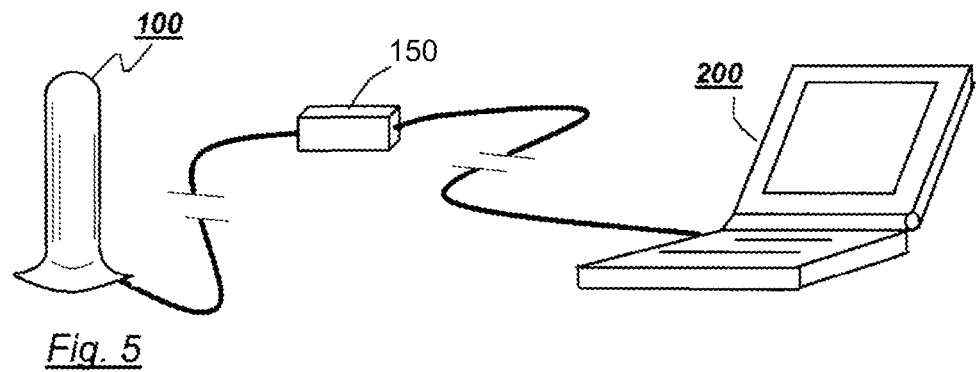
Fig. 5

APPARATUS, SYSTEM, AND METHOD FOR TESTING AND EXERCISING THE PELVIC FLOOR MUSCULATURE

PRIORITY CLAIM

This application claims priority to U.S. patent application Ser. No. 14/009,429, filed on Dec. 11, 2013, which is a 371 Application of PCT Application No. PCT/NO2012/050058, filed Apr. 3, 2012, which claims priority to Netherlands Patent Application No. 20110524, filed on Apr. 5, 2011, with each of the above applications being incorporated herein by reference.

BACKGROUND

The present invention relates to an apparatus, system, and method for testing and exercising the pelvic floor musculature.

The pelvic floor muscles are a mind-controlled and layered muscle group which surrounds the urethra, vagina, and rectum, and which, together with the sphincter muscles, functions to control these openings. This musculature also serves to support the urethra, bladder, and uterus, as well as to resist any increases in the abdominal pressure developed during physical exertion. The muscle group includes both longitudinal muscles and annular muscles.

Training of the pelvic floor musculature has proven efficient in preventing and treating several conditions, e.g. incontinence. Numerous exercises exist for training the pelvic floor musculature. For a number of reasons, the effect of these exercises varies among people. Also, it is known that mechanical vibrations in a range below approx. 120 Hz applied to the tissue increase the training effect of such exercises. As the musculature becomes stronger, it will be possible to measure the training effect by measuring the ability of the musculature to retract.

Measuring Principle and Measurement Parameters

A stronger muscle can be expected to dampen an amplitude of oscillation applied thereto more than a weaker muscle. A first principle of measurement, therefore, may be to measure the amplitude dampening of an imposed oscillation. The measured amplitude can be described as $A \sim A_0 \sin(wt)$. A relative amplitude dampening is defined as: where $$\Delta A = (A - Ao)/Ao \qquad (1)$$

A is the amplitude measured,
Ao is the amplitude imposed,
w is the angular frequency of the oscillation imposed, and
t is time.

It is considered well known to a person skilled in the art that the output signal from an accelerometer may represent an acceleration which can be integrated to obtain a velocity and a second time to obtain a displacement or deflection. It is also well known that accelerations, velocities, and displacements of equal magnitudes and opposite directions have average values of zero, and that meaningful parameters hence must be based on absolute values such as maximum acceleration, velocity, or amplitude, for example. In view of the above, it is clear that the dimensionless attenuation $\Delta A$ can be calculated from displacements in mm, velocities in m/s, accelerations in m/s$^2$, and/or electrical signals input to the oscillator and output from the accelerometer. In any case, the attenuation M can be expressed in dB, calibrated to display the force in Newton (N), etc. according to need and in manners known for persons skilled in the art.

During exercise, the volume of the muscle cells increases and the skeleton of the cells becomes more rigid. In another model, therefore, the pelvic floor musculature can be regarded as a visco-elastic material, i.e. as a material having properties between a fully elastic material and an entirely rigid and inelastic (viscous) material. For example, a slack or weak muscle can be expected to exhibit relatively "elastic" properties, whereas a tight or strong muscle can be expected produce more resistance and thus relatively "viscous" properties. Formally:

stress is the force acting to resist an imposed change divided by the area over which the force acts. Hence, stress is a pressure, and is measured in Pascal (Pa), and strain is the ratio between the change caused by the stress and the relaxed configuration of the object. Thus, strain is a dimensionless quantity.

The modulus of elasticity is defined as the ratio $\lambda$=stress/strain. The dynamic modulus is the same ratio when the stress arises from an imposed oscillation. When an oscillation is imposed in a purely elastic material, the elongation measured is in phase with the imposed oscillation, i.e. strain occurs simultaneously with the imposed oscillation. When the oscillation is imposed in a purely viscous material, the strain lags the stress by 90° ($\pi/2$ radians). Visco-elastic materials behave as a combination of a purely elastic and a purely viscous material. Hence, the strain lags the imposed oscillation by a phase difference between 0 and $\pi/2$. The above can be expressed through the following equations:

$$\sigma = \sigma_o \sin(\omega t) \qquad (2)$$

$$\varepsilon = \varepsilon_o \sin(\omega t - \phi) \qquad (3)$$

$$\lambda = \sigma/\varepsilon \qquad (4)$$

where
$\sigma$ is stress from an imposed oscillation (Pa)
$\varepsilon$ is strain (dimensionless)
$\omega$ is the oscillator frequency (Hz)
t is time (s),
$\phi$ is the phase difference varying between 0 (purely elastic) and $\pi/2$ (purely viscous), and
$\lambda$ is the dynamic module.

Biomechanically, this may be interpreted as that a stronger muscle increases the force resisting the oscillation and thereby "delays" the vibrations measured by the accelerometer. This is equivalent with that a strong muscle is stiffer or "more viscous" than a slack, gelatinous, and "more elastic" muscle.

A general problem in the prior art in the field is that measurement values are often given in terms of pressure, e.g. in millimeter water column. As pressure is a force divided by an area, the pressure reported will depend on the area of the measuring apparatus, and hence on the supplier. Therefore, in the literature in the field, measurement values are often given in the format '<Supplier_name> mmH2O', for example. In turn, this results in that measurement values from different apparatuses are not directly comparable, and consequently a need exists for supplier independent measurement values in the field of the invention.

U.S. Pat. No. 6,059,740 discloses an apparatus for testing and exercising pelvic floor musculature. The apparatus includes an elongate housing adapted for insertion into the pelvic floor aperture. The housing is divided longitudinally into two halves, and includes an oscillator as well as a cut out and equipment for measuring pressure applied to the housing halves from the pelvic floor musculature. The apparatus indicates the force pressing together the two halves in Newton (N), and essentially measures the training effect on muscles acting radially on the housing.

A need exists for an apparatus which also measures and trains the musculature running in parallel with a longitudinal direction of the apparatus or pelvic floor opening.

The object of the present invention is to address one or more of the above problems, while maintaining the advantages of prior art.

SUMMARY OF THE INVENTION

According to the invention, this is achieved by an apparatus for testing and exercising pelvic floor musculature, the apparatus including an elongate housing adapted for a pelvic floor opening, the housing including an oscillator, characterized in that the housing includes an accelerometer connected to a signal processor configured for communicating signals representative of values read from the accelerometer.

The use of an accelerometer for measuring a response makes it possible to use a closed housing, simplify the remaining construction, and increase the accuracy of the measurements. It is also possible to calculate a relative amplitude attenuation, phase delay, and/or dynamic modulus in one or more dimensions. These parameters, combined or individually, can be used for characterizing the musculature in a more accurately and detailed manner than is possible with the prior art.

Also, imposing oscillations and/or measuring responses along several axes allow the adaptation of training and testing to specific muscle groups in the pelvis floor.

In another aspect, the present invention relates to a system using such an apparatus with a controller configured for controlling the frequency and/or amplitude of the oscillation. The system is characterized in that it further includes a control module configured for determining an oscillator parameter within at least one time interval, and for providing the oscillator parameter to the controller; a data capturing module configured for receiving a response from the accelerometer and calculating a result as a function of the oscillator parameter and the received response; an analysis module configured for calculating at least one group value based on a series of measurements of oscillator parameters and the results thereof; a data storage configured for storing and retrieving at least one data value from a group consisting of the oscillator parameters, response, calculated result, and group value; and communication means configured for conveying the data value between the modules and the data storage.

In a third aspect, the present invention relates to a method for testing and exercising the pelvic floor musculature, wherein an oscillation is imposed on the musculature, characterized by measuring the response from the musculature using an accelerometer and characterizing the musculature based on the response to the oscillation imposed.

Suitable measurement parameters, such as the relative amplitude attenuation, phase delay, and/or dynamic modulus, may indicate, among other things, force and/or elasticity of various muscle groups in the pelvic floor.

In a preferred embodiment, the musculature is imposed an oscillation of a frequency equal or close to the maximum response frequency during training of the musculature. The maximum response frequency is assumed to change over time, and may be, inter alia, displayed and/or logged in order to document training effect, alone or in combination with one or more other parameters.

Additional features and embodiments will be apparent from the attached patent claims.

BRIEF DESCRIPTION OF THE DRAWINGS

The invention will be described in more detail in the detailed description below with reference to the appended drawings, in which:

FIG. 1 is a longitudinal schematic section of an apparatus;

FIG. 2 illustrates alignment of a triaxial accelerometer in the apparatus of FIG. 1;

FIG. 3 (prior art) shows the principle of an oscillator;

FIG. 4 (prior art) shows the principle of an accelerometer;

FIG. 5 is a schematic illustration of a system according to the invention;

DETAILED DESCRIPTION

Figure 6:
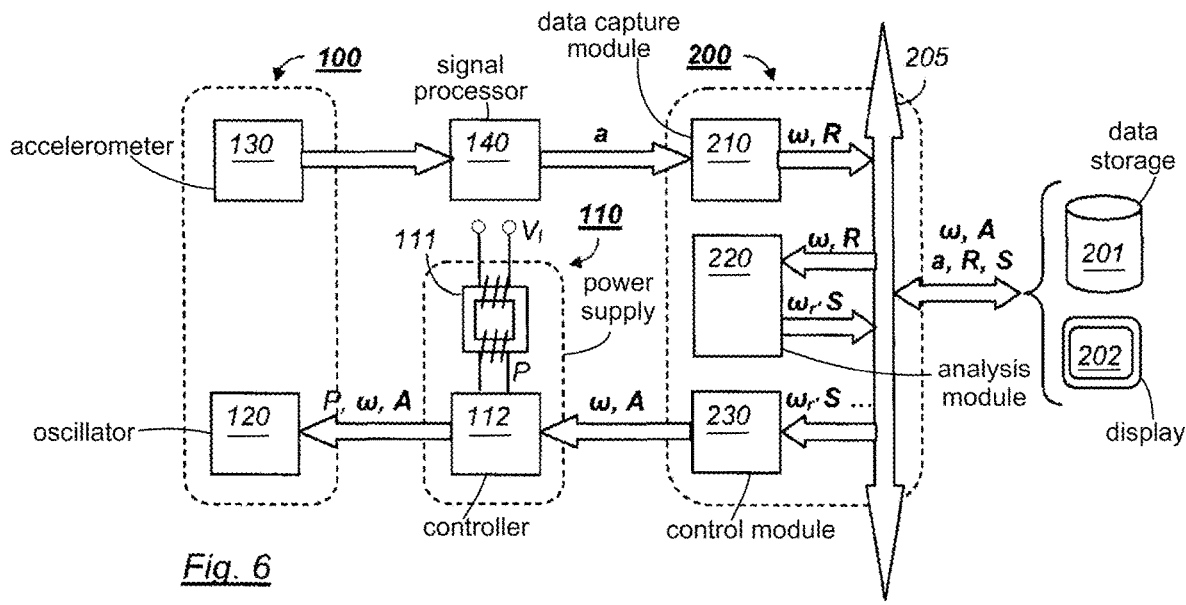
FIG. 6 is a schematic depiction of the functions of the system.

FIG. 1 is a longitudinal schematic section of an apparatus 100 according to the invention. The apparatus is comprised of an elongate, cylindrical housing 101, which can be made of a relatively rigid plastic material. Advantageously, an outer casing 102 made of medical silicone can be provided on the outside of housing 101. The size of the housing is adapted for an opening in the pelvic floor.

Housing 101 includes an oscillator 120 able to oscillate along one, two, or three axes, and an accelerometer 130 able to measure the acceleration along one, two, or three axes. Preferably, the accelerometer axis or axes is/are aligned with the oscillator axis or axes, for the following reason:

Assume that oscillator 120 effects an oscillation of the apparatus along an axis x, and that the response is measured along an axis x' forming an angle $\alpha$ with the x-axis. If a response along the x-axis is B, then the response along the x'-axis $B'=B \cdot \cos \alpha$. B' has a maximum for $\cos \alpha=1$, i.e. with $\alpha=0$ and the x'-axis parallel with the x-axis. Correspondingly, $B'=0$ when the accelerometer axis is perpendicular to the oscillation ($\cos 90°=0$). Thus, by arranging the x-axis of accelerometer 130 in parallel with the x-axis of oscillator 120 we expect the largest possible signal and hence the greatest sensitivity possible. The same is true along the y- and/or z-axes when apparatus 100 has more than one axis. Also, the level of crosstalk between the measured signals is minimized when the axes are perpendicular to each other, e.g. as shown with the x, y, z coordinate system of FIG. 1.

From FIG. 1 is can also be seen that oscillator 120 and accelerometer 130 are offset relative to each other along the longitudinal axis of the apparatus, i.e. the z-axis. Strictly speaking, therefore, they have separate axes in the x direction, e.g. x and x'. However, this has no significance as long as the axes are parallel to each other, cf. the previous section. Hence, for convenience, the x-axes of the oscillator, accelerometer and apparatus are referred to as one axis, "the x-axis". The same applies for the y- and z-axes.

FIG. 2 illustrates a triaxial accelerometer 130, having its axes x, y, and z parallel with the axes x, y, and z of the apparatus shown in FIG. 1. In a preferred embodiment, the frequencies of the oscillations, and optionally also the amplitudes, can be controlled independently of each other along said x, y, and z axes. This makes it possible to measure the strength of a muscle or muscle group running in parallel with the main axis of the apparatus, the z-axis, independently of muscles or muscle groups acting radially on the apparatus along a combination of the x- and y-axes of FIG. 1.

In the following, parameters of one, two, or three dimensions are denoted with boldfaced characters, and the component of a parameter along the x, y, and/or z axis is indexed with x, y, and z, respectively. For example, the frequency $\omega=(\omega_x, \omega_y, \omega_z)$. In some embodiments, the three frequency components may have different values, and one or two of the components can be zero, i.e. one or two oscillators could be eliminated. The same applies for a response or out signal a from accelerometer 130, calculated results $\Delta A$, $\varphi.A$, and so on. Components along the x, y, and z axes are measured and calculated independently of each other, e.g. as indicated in eqs. (1) to (4).

The oscillator 120 can be controlled to vibrate with a specific frequency, preferably within the range of 15-120 Hz, by a power supply 110. Alternatively, the oscillator 120 can be driven by a battery 111a, shown with broken lines in FIG. 1.

The output signal from accelerometer 130 can be passed to a signal processor 140 and thence to a computer 200 (see FIGS. 5 and 6). Alternatively, the entire or parts of the signal and data processing can be performed by a unit 200a inside the housing 101.

Oscillator 120, accelerometer 130, and signal processor 140 are commercially available products, and it is within the ability of a person skilled in the art to select models suited for the particular purpose. It is understood that FIG. 1 is a principle drawing, and that the connections between the components may include several channels, e.g. one input channel per oscillator axis and one output channel per accelerometer axis. In some applications, accelerometer 130 and/or signal processor 140 may be driven by electric power supplied through a USB connection, for example. In other applications, it may be necessary or convenient to have a separate grid-connected transformer 111 in the power supply 110, as shown in FIG. 6.

FIG. 3 illustrates the principle of a possible oscillator 120. The oscillator shown includes a permanent magnet 126 arranged in a coil 125. When an AC voltage Vx is applied to the poles and a current is driven through the coil, a variable magnetic field is induced which drives the permanent magnet 126 back and forth in a reciprocating motion. The permanent magnet 126 is attached to a weight 122 which hence also moves back and forth. When the oscillator is attached to housing 101, the apparatus 100 will oscillate along the x-axis.

FIG. 4 illustrates the principle of a typical accelerometer. A piezoelectric disc or bar 133 is fixedly clamped within a housing 131. The disc 133 retains a seismic mass 132.

When the housing is moved back and forth along the x-axis, the disc will be acted on by the mass 132 and an electric charge is produced, typically a few pC/g, on the disc 133 by the piezoelectric effect. For frequencies below about one third of the resonance frequency of the accelerometer housing, this charge will be proportional with the acceleration. The output signal is illustrated schematically as $\alpha_x$ in FIG. 4. Commercial vibrational testing accelerometers of this type typically have a frequency range from approx. 0.1 to above 4 kHz, i.e. far outside the range of 15-120 Hz preferred in the present invention.

The present invention does not rely on any specific types of oscillators or accelerometers. For example, eccentric weight oscillators may be used instead of the type shown schematically in FIG. 3. A design of the type shown in FIG. 3 can also be used as an accelerometer: In such a case, weight 122 is moved in dependency of the applied forces. This induces a movement of permanent magnet 126 inside coil 125, and a current is induced that can be read at the poles at $V_x$.

FIG. 5 illustrates a system in which a computer 200 controls an oscillator of apparatus 100 through a power supply 110. The computer 200 can be of any design. Suitable computers have a programmable processor, and include personal computers, portable units (PDAs), etc. Computer 200 can be connected to a display, printer, and/or data storage in a known manner for displaying and/or logging measurement results.

Signals from an accelerometer (130, FIG. 1) of apparatus 100 are amplified and/or processed in a signal processor 140 and transferred to computer 200 for analysis and/or logging. The connection between apparatus 100 and the box 110, 140 may include several channels for controlling oscillators along several axes independently of each other as well as for measuring responses of a uniaxial or multiaxial accelerometer. The same applies for the connection between box 110, 140 and computer 200. This connection may be a USB (2.0 or the like) connection, and, in some applications, electric power may be supplied from the computer through the USB connection.

In some embodiments, signals may be transferred wirelessly (not shown), e.g. by way of radio signals, infrared light, or ultrasonic signals.

Figure 8A:
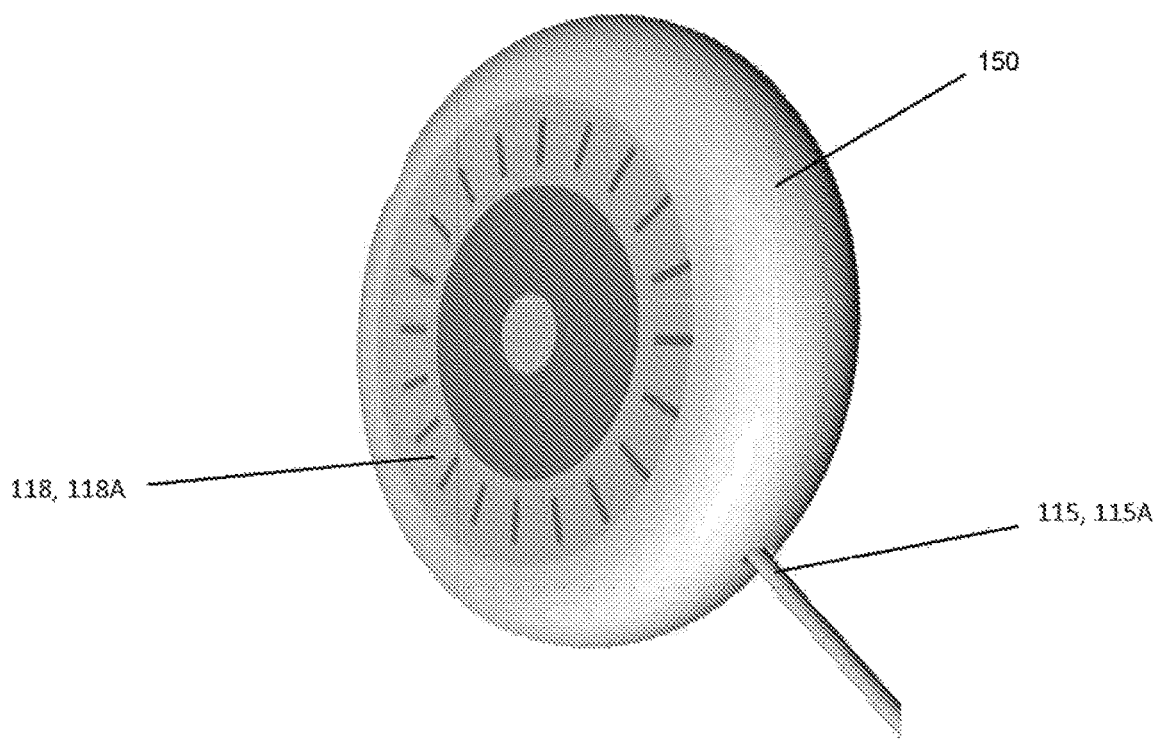
FIGS. 8A-8D illustrate a more detailed embodiment of the signal processor according to the invention.
Figure 8B:
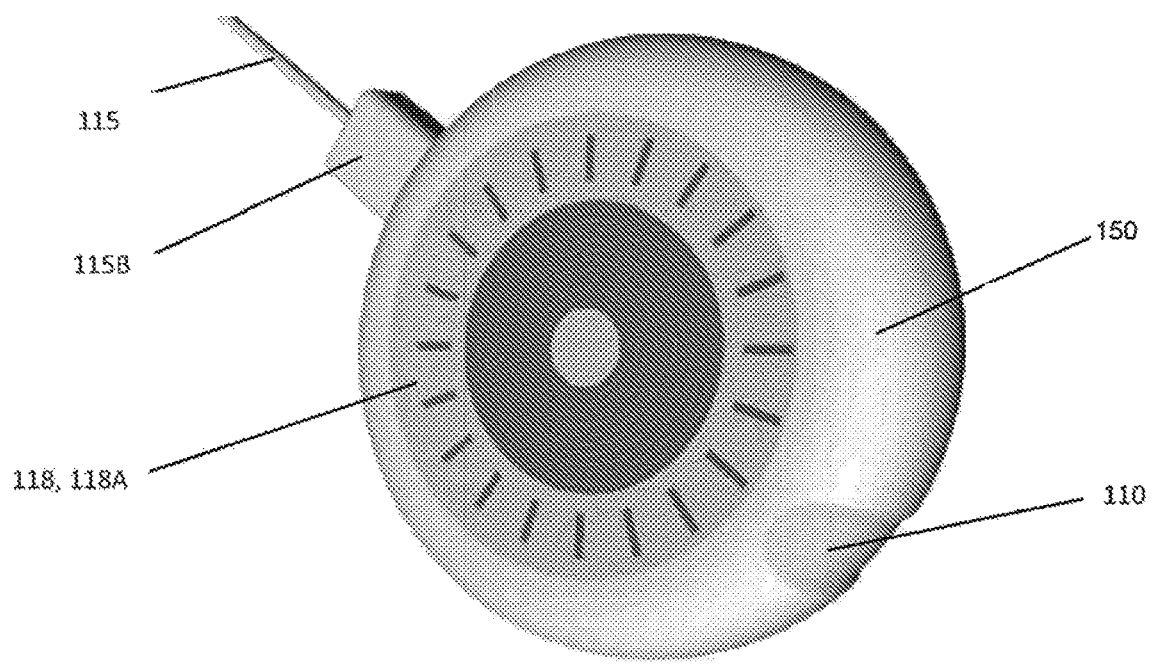
Figure 8C:
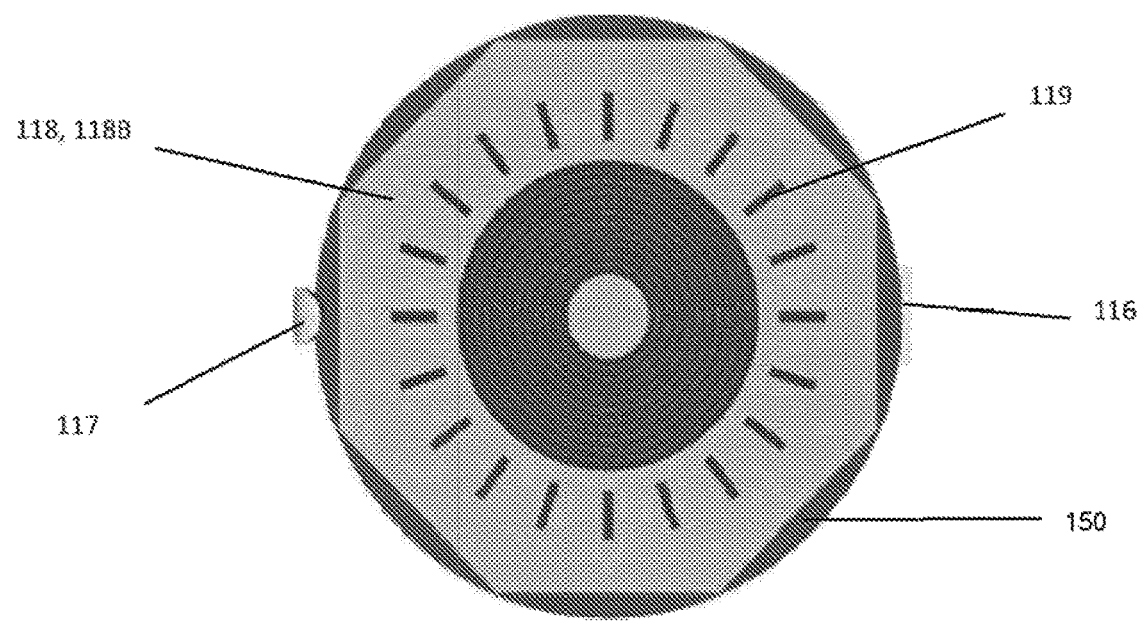
Figure 8D:
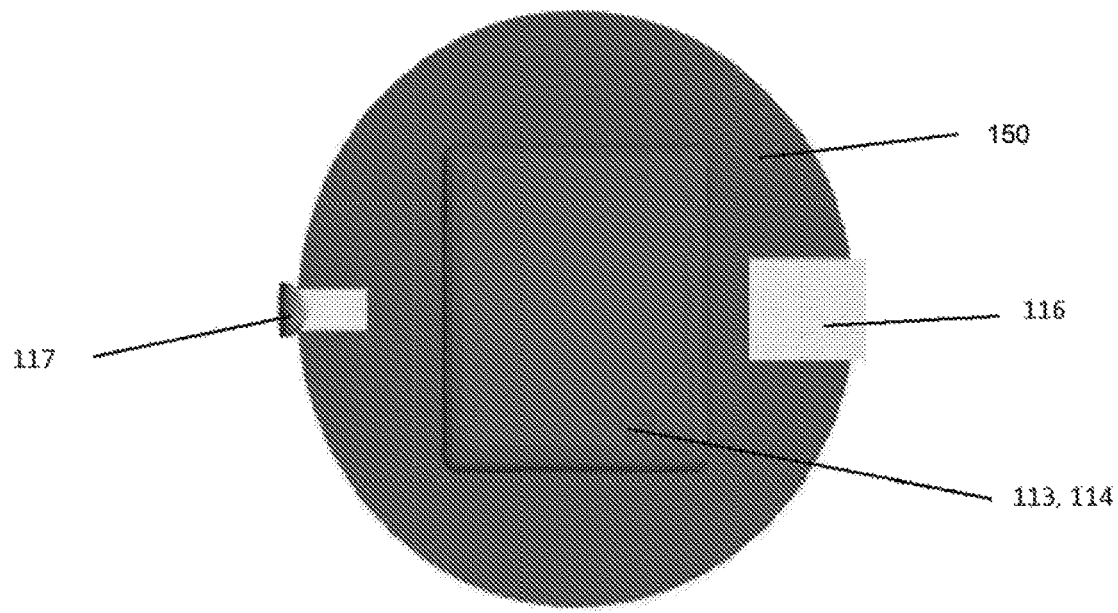

FIGS. 8A-8D show another embodiment of the system, and in particular a more detailed embodiment of signal processor 110, 140, according to the present invention, in which the power supply 110 and signal processor 140 can be embedded into a separate unit or box 150 accommodating at least one rechargeable or replaceable battery or battery package 113 (FIG. 8D).

Signal processor 140 may also include: a CPU including the appropriate software; electronic circuitry programmed with suitable algorithms for managing and controlling the oscillation frequency and optionally the oscillation amplitude; input(s) for at least one EMG sensor (EMG= Electromyography); and input(s) for at least one force sensor.

The stand-alone unit or box 110, 140 can include a charge input. Additionally to the charge input, or in an alternative embodiment, in which the battery or batteries or the battery package 113 is to be replaced or charged at another location, the stand-alone unit or box 110, 140 may include a cover 114 which can be opened and closed, or the casing (housing) of the unit or one half of the unit or box 110 may be arranged so as to be easily opened and closed (i.e. without the need for using a tool).

The wire 115 from apparatus 100 may be permanently connected 115A to the box 110 of signal processor 140, or, alternatively, may be arranged so as to be pluggable 115B (by means of a plug 115B) into the input port or connector 116 of the unit 110, 140.

Signal processor 140 may further include a loudspeaker and/or display 118 for the instantaneous or immediate biofeedback on muscle activation as observed through the dampening of oscillations and/or force read from the apparatus 100 and/or EMG activity in the muscle acting on apparatus 100. Display 118 may have a suitable shape adapted for the requirements of functionality and placement. An octagonal (eight-sided) 118B, six-sided or round 118A LCD or LED display 118, having about 40 segments 119, for example, could be used. The unit 110, 140 may also include an on/off button 117. In addition, or alternatively, the electronic circuitry of signal processor 140 may be configured so as to switch off after a predetermined time interval of inactivity, e.g. from one to a few minutes of no active use.

Additionally, the stand-alone unit or box 110, 140 may include a CPU device and/or calibration means including at least one of a CPU device and various sensor means to allow, among other things, the calibration of a new apparatus 100 in the system. Unit 110, 140 may also transfer, e.g. wirelessly, real-time data to computer 200 of various reasons.

Apparatus 100 may include an integrated triaxial gyro sensor 160 which, together with the triaxial accelerometer 130, allows the data or signal processor 140 or computer 200 to calculate the 3D orientation of the apparatus 100.

FIG. 6 is a schematic depiction of components of the system illustrated in FIG. 5.

A control module 230, e.g. hardware and software in the computer 200, determines an oscillator parameter, i.e. frequency and/or amplitude, for oscillator 120. When the apparatus is being used for the first time, the control module 230 could set the frequency $\omega$ to a fixed initial value and then increase the frequency in predetermined increments $\Delta\omega$. On subsequent use, control module 230 can use previous results for selecting other initial values and/or frequency intervals. This is described in more detail below. The same applies for the amplitude settings. Alternatively, oscillator parameters could be determined in a binary search which is ended when the values of two consecutively calculated values are closer than a predetermined resolution, e.g. $\Delta\omega_x = 5$ Hz.

Both frequency and amplitude may be adjusted along the x, y, and z axes independently of each other by means of controller 112. In FIG. 6, controller 112 is connected to a power source in the form of a transformer 111 connected to the grid voltage $V_l$, delivering a power P with the desired current and voltage. As shown in FIG. 1, in the alternative, the power source could be a battery 111a located inside the housing 101 of the apparatus. For example, the controller 112 may control the amplitude $A_x$ and frequency $\omega_x$ of the oscillator by controlling the current, voltage, and frequency of the signal supplied at the poles Vx of FIG. 3, and in a similar manner for oscillators oscillating along the y and/or z axes.

The oscillation is imposed on tissue surrounding apparatus 100, and the response is measured by accelerometer 130.

Signals from accelerometer 130 of apparatus 100 are passed to a signal processor 140, which is provided as a separate box including an array of accelerometers. Accelerometer 130 may include a preamplifier, and unit 140 may include a pre-amplifier. Other configurations are possible as well. The output signal from signal processor 140 is shown as a, and may represent, for example, acceleration along the x, y, and/or z axes at a measurement point at which the imposed oscillation was $\omega_i$.

A data capturing module 210 process the signal further, and may, for example, integrate an acceleration to obtain a velocity and once more to obtain a displacement, measure a phase difference, etc. Said integration of acceleration, measurement of phase difference, etc. may be carried out at several locations in the signal path using feedback operational amplifiers, firmware, and/or software, for example, in a known manner. Note that the signal path of FIG. 6 is exemplary only.

Output data from the data capturing module 210 are shown schematically as a measurement point $\omega$, R, at which a result R is measured or calculated at an applied frequency $\omega$. The result R may represent one or more of: acceleration $\alpha$, velocity, displacement, relative amplitude attenuation $\Delta A$, phase shift, stress, strain, and/or dynamic modulus as discussed above. In some applications, the oscillator amplitude may also be varied. Advantageously, the data capturing module can store a measurement sequence including a series of measurement points each representative of an oscillator parameter $\omega$ or A and a measured or calculated result R. As used herein and in the claims, the term "data values" is understood to mean any parameter value and/or the components thereof along the x, y, and/or z axes.

A data bus 205 carries data values between various components and modules of computer 200. For example, a measurement series with a sequence of measurement points $(\omega_i, R_i)$ can be temporarily be stored in a data storage 201 before the measurement series is further processed in an analysis module 220. In another embodiment, the measurement points $(\omega_i, R_i)$ could be passed to analysis module 220 at a later point, and the processing results, represented by $(\omega_r, S)$, could be stored in data storage 201 and/or displayed on a display means 202.

Analysis module 220 is a module processing one or more measurement series to characterize the musculature and the development thereof using one or more parameters deemed suitable.

In a preferred embodiment, a maximum response frequency $\omega_r$ is obtained for each measurement series. The maximum response frequency $\omega_r$ is the value of the imposed frequency for which the measurement parameter selected indicated a maximum response from the tissue surrounding the apparatus, such as the maximum amplitude attenuation, minimum amplitude measured, largest dynamic modulus, etc. This is discussed in more detail below.

In principle, analysis module 220 may calculate any desired group value and/or carry out statistical analysis of the acquired data, such as statistical distributions, mean or expected value, variance, maximum values, and trends in the development of the measured and calculated results described above, for example.

In one embodiment, for example, the group value S may represent a subinterval of the range of 15-120 Hz within which the maximum response frequency $\omega_r$ is located with a given probability. This interval may be calculated as a confidence interval from earlier measurement series using known statistical methods, and is expected to become smaller as the number of measurement series increases and the variance hence reduces. The purpose of calculating such a subinterval is to avoid superfluous measurements.

An exemplary trend analysis is the development of the maximum response frequency $\omega_r$ over a few days or weeks, which may provide information on training effect.

Figure 7:
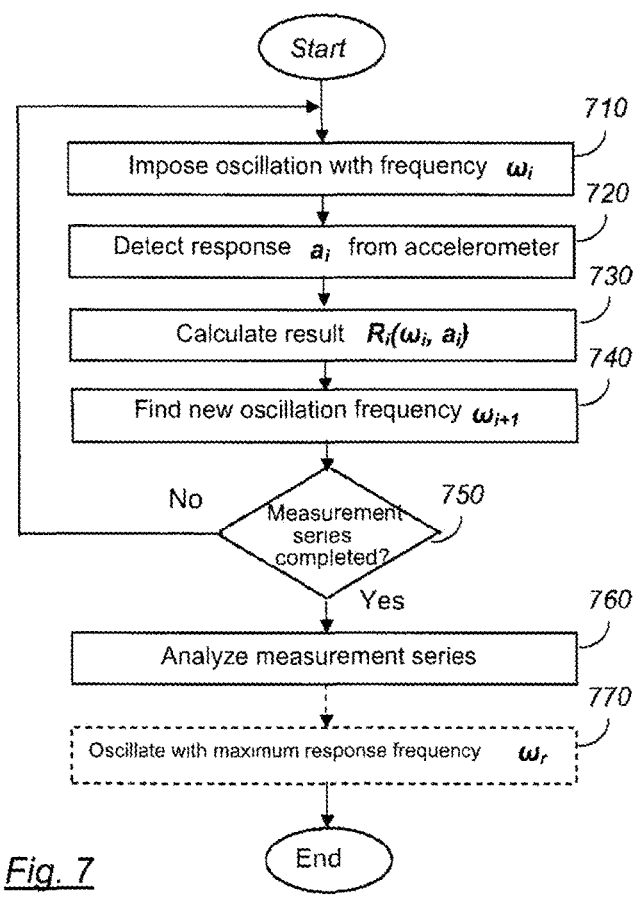
FIG. 7 is a flow diagram illustrating a method according to the invention.

FIG. 7 illustrates a method according to the invention.

In block 710, the musculature is imposed a first oscillation represented by $\omega_i$. In practice, this can be accomplished by introducing an apparatus as described above into a pelvic floor aperture and supply the oscillator 120 with electric power. The oscillation may be imposed along one or more mutually orthogonal axes (x, y, z). At the first use, the initial value could be about 15 Hz, for example, along each axis. After the apparatus has been used one or more times the initial values may be based on previous results and analyses.

In block 720, the response $\alpha_i$, from the musculature is measured by means of an accelerometer 130 having axes oriented in parallel with the oscillator axes x, y, and/or z.

Block 730 illustrates that a result $R_i$ is found from an imposed oscillation $\omega_i$ and its response $\alpha$; as measured in a predetermined time interval. The measurement point $(\omega_i, R_i)$ may be part of a measurement series in which i=1, 2, ... n, and each index i represents a separate time interval. Both the imposed frequency and the measured or calculated result have distinct values along the oscillator axes. Results suitable for characterizing the musculature may be the relative amplitude attenuation ΔA, dynamic modulus λ, and/or phase shift φ between the applied and measured signals. The values may be measured and/or calculated as set out above in connection with eqs. (1) to (4), and independently of each other along the axis or axes x, y, and/or z. The measurement point $(\omega_i, R_i)$ can be stored or logged as part of this step.

In block 740 an oscillation frequency for the next measurement point is calculated, and in determination block 750 a determination is made whether the measurement series has been completed.

In a first embodiment of the method, the imposed frequency is incrementally increased in block 740, for example according to $\omega_i = \omega_0 + i \cdot \Delta\omega$, where $\Delta\omega$ denotes a desired resolution for the measurement series, such as 1 Hz or 5 Hz. In this case, the loop ends in determination block 750 when the new frequency $\Delta\omega_{i+1}$ exceeds a predetermined threshold, e.g. 120 Hz, along the axis or axes.

In an alternative embodiment of the method, the objective is to find a maximum response using the smallest number of measurements possible. This may be carried out efficiently by way of a binary search. For example, assume that the result R from block 730 increases with the response of the musculature to the imposed oscillations, that a first interval is 15 Hz to 120 Hz, and that the desired resolution is 5 Hz along each axis. In this case, the binary search can be performed by bisecting the interval, rounding the frequency down to the nearest integer frequency divisible with the resolution, and compare the results of block 730 for each of the two frequencies in the upper and lower parts of the interval, e.g. $R_1$ at $\omega_1=15$ Hz and $R_2$ at $\omega_2=50$ Hz. If R2>R1, $\omega_3$ is selected as the center of the interval 50-120 Hz in block 740, otherwise $\omega_3$ is selected as the center of the interval 15-50 Hz in block 740. Similar bisection of the intervals is repeated in this alternative embodiment until determination block 750 indicates that the next interval is narrower than the desired resolution, e.g. 5 Hz along each axis.

If the responses along the axes are independent of each other, a binary search in the interval 15-120 Hz with a resolution of 5 Hz along each axis will be able to find an approximate maximum response frequency using at most 6 measurement points, whereas a sequential search in the interval 15-120 Hz with a resolution of 5 Hz would require 21 measurement points.

If determination block 750 indicates that the measurement series has not been completed, a new iteration is performed in which block 710 imposes an oscillation with a new frequency $\Delta\omega_{i+1}$, etc. When determination block 750 indicates that the measurement series has been completed, the process proceeds to block 760.

In block 760 one or more measurement series is analyzed as described for analysis module 220 above. In a preferred embodiment, the maximum response frequency $\omega_r$ is calculated for each measurement series. By definition, this is the frequency at which the musculature responds most strongly to the imposed oscillation. In practice, the maximum response frequency can be rounded down to the nearest integer frequency which is divisible with the resolution, i.e.

$$\omega_r = \Delta\omega \cdot \text{round}(\omega_r'/\Delta\omega), \quad (5)$$

where
$\omega_r$ is the practical value of the maximum response frequency,
$\omega_r'$ is the theoretical or ideal value of the maximum response frequency,
$\Delta\omega$ is the resolution chosen, e.g. 5 Hz as in the above example, and
round( ) is a function which rounds down to the nearest integer.

Block 770 has been drawn with dashed lines to illustrate that the method may, but does not necessarily, include controlling the oscillator to impose the practical value for the maximum response frequency while a user performs pelvic floor exercises as described in the introductory section. Hence, in a preferred embodiment, the resolution $\Delta\omega$ should be selected so that the difference between the practical and actual values is of little or no significance. For example, if it turns out to be a telling difference between training with an imposed oscillation of 62 Hz as compared to 60 Hz, $\Delta\omega$ in the above example should be reduced from 5 Hz to 1 Hz.

The method may further include storing and/or displaying one or more oscillation parameters, measurement values, calculated results, and/or group values. Each data value may be stored in a data storage 201 and displayed on a monitor 202. It is also possible to log parameters by printing them on paper. Hence, a printer (not shown) may optionally be used instead of or in addition to data storage 201 and display 202 (e.g. a monitor) shown in FIG. 6.

The method described above may further include analyzing the measured and calculated results using known statistical methods. In one embodiment, the development of the maximum response frequency and/or other results over time, for example, may document the training effect. Also, in the present or other applications, a confidence interval for $\omega_r$ can be estimated which is smaller than the entire measurement interval, e.g. 15-120 Hz, but still large enough for the probability p that the maximum response frequency is located within said interval to be larger than a predetermined value, such as p>95%.

This may reduce the number of measurement points in the next measurement series, which may be recorded one or a few days later, for example, and stored in data storage 201 (FIG. 6). Data storage 201 may store several such measurement series recorded during a time period, e.g. one measurement series per day for 1-4 weeks, and/or only the particular frequency $\omega_r$ within each measurement series which resulted in, for example, the maximum amplitude attenuation or phase shift.

Naturally, statistical analysis, trend analysis, etc. may be performed on one or more measured or calculated results, not only on the frequency as described above. The expression "calculating group value", as used in the patent claims, is intended to include any known types of statistic analysis, trend analysis as well as other forms of analysis performed on one or more measured or calculated results, stored, for example, as measurement series of measurement points $(\omega_i, R_i;)$ in data storage 201.

The invention claimed is:

1. A system for increasing pelvic tissue volume, the system comprising:
   a probe having an elongate housing with an interior, an oscillator and an accelerometer operatively positioned therein;
   a control module configured for determining an oscillator parameter within at least one time interval, and for providing the oscillator parameter to a controller of the probe;
   a data capturing module configured for receiving an amplitude signal and an attenuation of the amplitude signal from the accelerometer and calculating a result as a function of the oscillator parameter and the received attenuation of the amplitude signal; and an analysis module configured for conducting an analysis based on a measurement series of oscillator parameters and results thereof;

wherein the attenuation of the amplitude signal correlates to a volume of pelvic tissue cells.

2. The system of claim 1, wherein the volume of pelvic tissue cells correlates to a visco-elastic property of the pelvic tissue.

3. The system of claim 1, further comprising a data storage configured for storing and retrieving at least one data value from a group consisting of: the oscillator parameters, the signal from the accelerometer, the calculated result, and a result of the analysis module; and communication means configured for conveying the at least one data value between the control module, the data capturing module, the analysis module and the data storage, wherein the controlled oscillations of the oscillator are controlled with respect to the signal from the accelerometer.

4. The system of claim 1, further comprising a display configured for displaying the at least one data value.

5. The system of claim 4, wherein the display is at least one selected from the group of a visual display, an audio display, or a combination of a video display and an audio display.

6. The system of claim 4, wherein the display is a wireless display.

7. The system of claim 1, wherein an output from the analysis module is selected from a group consisting of: a maximum response frequency and a subinterval of a frequency range of 15 to 120 Hz.

* * * * *